(12) United States Patent
Anitua

(10) Patent No.: US 7,144,428 B2
(45) Date of Patent: Dec. 5, 2006

(54) METHOD FOR SURFACE TREATMENT OF IMPLANTS OR PROSTHESIS MADE OF TITANIUM OR OTHER MATERIALS

(76) Inventor: Eduardo Aldecoa Anitua, San Antonia, 15 E-01005, Vitoria (ES)

( * ) Notice: Subject to any disclaimer, the term of this patent is extended or adjusted under 35 U.S.C. 154(b) by 96 days.

(21) Appl. No.: 10/203,426

(22) PCT Filed: Sep. 14, 2001

(86) PCT No.: PCT/ES01/00348

§ 371 (c)(1),
(2), (4) Date: Feb. 14, 2003

(87) PCT Pub. No.: WO02/24243

PCT Pub. Date: Mar. 28, 2002

(65) Prior Publication Data

US 2003/0135282 A1   Jul. 17, 2003

(30) Foreign Application Priority Data

Sep. 19, 2000  (ES) ............................... 200002267
Jul. 13, 2001  (ES) ............................... 200101362

(51) Int. Cl.
*A61F 2/28* (2006.01)

(52) U.S. Cl. .................. 623/23.53; 623/923; 427/2.26
(58) Field of Classification Search ............. 623/23.53; 427/2.26
See application file for complete search history.

(56) References Cited

U.S. PATENT DOCUMENTS

| 4,330,891 | A | * | 5/1982  | Branemark et al. ...... 623/23.61 |
| 5,507,813 | A | * | 4/1996  | Dowd et al. ............. 623/23.63 |
| 5,863,201 | A | * | 1/1999  | Lazzara et al. .......... 433/201.1 |
| 5,876,453 | A |   | 3/1999  | Beaty |
| 5,986,168 | A | * | 11/1999 | Noishiki .................... 424/422 |

FOREIGN PATENT DOCUMENTS

| WO | WO 200024363 A1 | * | 5/2000 |
| WO | WO 00/50102 |   | 8/2000 |

\* cited by examiner

*Primary Examiner*—Brian E. Pellegrino
(74) *Attorney, Agent, or Firm*—Browdy and Neimark, PLLC

(57) ABSTRACT

A section of the implant is treated successively and separately with three different acids—hydrofluoric, sulphuric and hydrochloric acid— to create evenly distributed peaks on the surface and sufficient surface area. Plasma rich in growth factors is then applied to said surface.

5 Claims, No Drawings

METHOD FOR SURFACE TREATMENT OF IMPLANTS OR PROSTHESIS MADE OF TITANIUM OR OTHER MATERIALS

FIELD OF THE INVENTION

In general terms the invention concerns implants and prostheses in titanium and other materials. More specifically it concerns a method used in surface treatment of implants and prostheses and the surface obtained with this method.

The invention also concerns the surface treatment of any type of titanium stem prosthesis to be inserted into or resting on bones, such as hip or knee prostheses, implants, screws or osteosynthesis systems.

BACKGROUND OF THE INVENTION

It is already known to employ the general method of roughening the surface of titanium implants and the endosteal stems of various prostheses to increase implant-to-bone contact and thus make the surface more osteoconductive.

Among the processes used heretofore to improve the surface of these titanium implants, surface treatments using a mixture of sulphuric acid and hydrochloric acid as well as physical treatments such as surface blasting with different particles of different grain sizes and hardness are well known. These systems, however, do not create the desired high uniform roughness on the entire implant surface and, furthermore, particle-blasting treatments often leave uncontrolled grit residue on the titanium.

Reference U.S. Pat. No. 5,603,338 of 1994 concerns the surface treatment of titanium dental implants in which the implant is first blasted with materials of different grain sizes before being treated with hydrofluoric acid to remove the native oxide on the titanium surface. Finally the surface is treated with a mixture of sulphuric and hydrochloric acid.

Reference U.S. Pat. No. 5,876,453 of 1994 produced by the same patent holder as the foregoing reference, and also originating from initial application Ser. No. 351,214 concerns a dental implant where the surface has been treated using the technique described in the paragraph above, in which the upper section of the implant has a mechanically-polished surface and the threaded section of the implant has a rough, treated surface.

In accordance with the content of these two references, the rough implant surface is more uniform than that achieved using traditional techniques and consists of a surface with a uniform series of cone-shaped irregularities with heights ranging from 0.3 to 1.5μ.

With regard to the foregoing and more specifically to treatment whereby said surface is blasted initially with materials of different grain sizes, it has been proven that blasting of said surface, wherein compression causes a change in the physical structure, compacts it and makes it less permeable when attacked by acids and other subsequent treatments.

Blasting using materials of different grain sizes is, therefore, considered an inadequate treatment as it prevents a higher incidence of irregularities on the rough implant surface being obtained.

Similarly, and in line with suggestions put forward by Dennis P. Tarnow in an article entitled "Dental Implants in Periodontal Care", published in 1993 in "Current Science" (p 157–162), consideration is given to the possibility of protection provided by a mechanically-polished safety area in dental implants in order to prevent possible peri-implant disease. Such an invention is known as a hybrid implant.

WO-A-00/44314, filed by the applicant himself, concerns taking blood —in situ— from the patients themselves to create plasma and to then use this plasma to help the bone regenerate as quickly as possible.

SUMMARY OF THE INVENTION

It is an object of the invention of a method of surface treatment of implants and prostheses made of titanium and other materials to provide greater depth and homogeneity in the surface roughness of these implants in order to facilitate osseointegration.

Another object of this invention is to find a method whereby the bone regeneration process is speeded up.

In order to achieve this basic objective of the invention, claims are made regarding successive treatments of the endosteal section of the implant with three different acids to eliminate the previous blasting and with the protection, or otherwise, of a mechanically-polished safety area in the case of dental implants, knee or hip prostheses, etc. as in this case it would not be advisable to have a osteoconductive surface beyond the endosteal area.

Thus, the section of the implant that is to be treated is etched first of all with hydrofluoric acid at, for example, 15% concentration and for a period of approximately 15 seconds.

The surface is then etched for a second time, this time with sulphuric acid at a concentration of 97%, at a temperature of 70° C. and for a period of 3 minutes. These parameters can be set even higher if necessary.

A third and final etching is carried out using hydrochloric acid at 36.5%, at 70° C. and for 3 to 5 minutes. These parameters can be set even higher if necessary.

Finally the implant surface is neutralised with sodium carbonate for 5 to 30 seconds and without being shaken before being finished with successive washings of deionised water. Ultrasound treatment can be used if necessary.

It has been proven that in the successive application of these three acids each acid acts to form a separate surface, thereby creating greater surface area, as the peaks formed are more uneven, having an average height that ranges from 0.2 to 10 microns.

This undoubtedly makes more surface area available to optimise correct implant osseointegration and leads to better osteoconduction and retention of fibrin clots or plasma rich in growth factors.

Detailed Description of the Invention

As posited by Tarnow in 1993 the implant obtained in accordance with the invention has a mechanically-polished upper section, which extends up to an adjoining section in the threaded area of the implant, while the remainder of the threaded section up to the apical end will be etched.

The apical end, implant taper or self-threading screw can be protected or not, and not be etched to thus prevent the apical end being lost.

In general terms, emphasis is given here to the positive effects of etching the implant stem or the threaded or unthreaded section of the implant to be inserted into the bone, while the remainder of the implant will be left unetched so as not to create more osteoconductive surface than is necessary.

Furthermore, and returning to the foregoing, when both the surface-activated implant and the plasma are used separately in the treatment the bone regeneration process is speeded up.

The efficiency of both techniques has been demonstrated in a countless number of practical applications, in which it has been noted how the use of these techniques, when applied separately, leads to a considerable reduction in the time the bone needs to regenerate.

Surprisingly, it has been discovered that far from there being disadvantages when both techniques are used in conjunction with each other, there are, in fact, many genuine advantages. The correct combination of these methods leads to a significant increase in bioactivity, to such an extent that activity and the speed of patient bone regeneration is doubled in some cases.

It has thus been discovered that by placing the section of the surface of an implant or prosthesis —either made of titanium or other materials— that is normally activated in contact with a layer or coating of plasma rich in growth factors, obtained from the blood of the implant recipient, and which has been applied immediately prior to contact, the surface potentiality of the unit is doubled. What this means is that the time needed for osseointegration is cut by half. In addition, bone apposition is improved, i.e. there is increased bone-to-implant or bone-to-prosthesis contact.

The reason behind this surprising change in the surface activity of the implant or prosthesis has yet to be clearly established. It is believed that it is caused by the presence of fibrin bridges created by the plasma and by the concentration of growth factors. What is undeniable, however, is the improvement that results from using this technique; an improvement that can be clearly demonstrated when the technique is used.

This bioactivation process can be set in motion simply by immersing the implant in plasma and then placing the surface of the implant in contact with the bone by inserting it in the alveolus or cavity in question.

The surface coating can also be obtained by placing plasma inside the alveolus so that when the implant is inserted it comes into contact with the plasma.

The combination of both techniques would obviously produce the same results.

The basic claim of the invention, therefore, can be summarised as follows:

An implant or prosthesis wherein the surface is activated using acid, chemical or physicochemical surface treatments and which performs significantly better than other non-activated implants because of the rough and moisturising quality of the surface.

Nevertheless, an implant or prosthesis previously activated according to the aforementioned technique is effectively bioactivated if the surface of said implant or prosthesis is coated with a film of plasma rich in growth factors.

The time required for osseointegration is cut by half and bone apposition is improved and extended.

The invention claimed is:

1. In a method for increasing osteointegration speed of implants and prostheses made of titanium or other materials, where the implants and prostheses are to be inserted into an alveolus or bone cavity of a patient, wherein the implants and prostheses comprise an upper section, a threaded section and an apical end, wherein the upper surface and the threaded section are polished, the improvement comprising:
   a. treating the implant successively and separately with 15% hydrofluoric acid for a period of 30 seconds to form a first surface, 97% sulfuric acid at 70° C. for three minutes to form a second surface, and 36.5% hydrochloric acid at 70° C. for between three and five minutes to form a third surface;
   b. neutralizing the surfaces of the implant with sodium carbonate for five to thirty seconds, in the absence of shaking;
   c. washing the implant with deionized water with optional ultrasound treatment; and
   d. coating the surfaces of the implant or prosthesis with a layer of plasma rich in growth factors that has been obtained from the blood of the patient.

2. The method according to claim 1 wherein the rough surface of the implant or prosthesis is coated with the plasma rich in growth factors prior to being inserted into an alveolus.

3. The method according to claim 1 wherein a bioactive surface on the implant or prosthesis is created by placing plasma inside the alveolus so that when the implant or prosthesis is positioned in a patient, the plasma contacts and coats the rough surface of the implant or prosthesis.

4. The method according to claim 1 wherein a bioactive surface is created by coating the rough surface of the implant or prosthesis with the plasma and then inserting the implant or prosthesis into an alveolus into which plasma has been placed prior to insertion.

5. The method according to claim 1 wherein both the concentration of acids used and the time for applying the acids on the required surface of the implant or prosthesis is increased to etch the surface of the implant or prosthesis more deeply.

* * * * *